US009974426B2

(12) United States Patent
Ogawa et al.

(10) Patent No.: US 9,974,426 B2
(45) Date of Patent: May 22, 2018

(54) MASTER-SLAVE SYSTEM FOR MOVING SLAVE UNIT BASED ON MOTION COMMANDS INPUTTED INTO TWO COMMAND INPUT UNITS HELD BY EACH HAND OF OPERATOR

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 353 days.

(21) Appl. No.: 14/842,045

(22) Filed: Sep. 1, 2015

(65) Prior Publication Data
US 2016/0058514 A1 Mar. 3, 2016

Related U.S. Application Data

(63) Continuation of application No. PCT/JP2014/051292, filed on Jan. 22, 2014.
(Continued)

(51) Int. Cl.
*A61B 1/00* (2006.01)
*B25J 3/04* (2006.01)
(Continued)

(52) U.S. Cl.
CPC .......... *A61B 1/00045* (2013.01); *A61B 1/005* (2013.01); *A61B 1/00087* (2013.01);
(Continued)

(58) Field of Classification Search
CPC ............ A61B 1/00006; A61B 1/00087; A61B 1/00133; A61B 1/00149;
(Continued)

(56) References Cited

U.S. PATENT DOCUMENTS 3,806,673 A * 4/1974 Boulanger ............... G06C 7/02
200/17 R
6,120,433 A * 9/2000 Mizuno .................. A61B 34/70
600/102
(Continued)

FOREIGN PATENT DOCUMENTS

JP H08-215211 A 8/1996
JP 2002-187078 A 7/2002
(Continued)

OTHER PUBLICATIONS

International Search Report dated Apr. 28, 2014 issued in PCT/JP2014/051292.

*Primary Examiner* — John P Leubecker
(74) *Attorney, Agent, or Firm* — Scully, Scott, Murphy & Presser, P.C.

(57) ABSTRACT

There is provided a master-slave system including: a slave unit including an observation optical system imaging a subject A; a treatment part projecting from a surface on which the observation optical system is provided and at least part of the treatment tools is imaged along with the subject A by the observation optical system; a master apparatus including an operating unit held and operated by an operator; a control unit associating operation of the operating unit of the master apparatus with motion of the slave unit and motion of the treatment part; and a monitor screen displaying an image acquired by the observation optical system, wherein the operating unit includes a command input unit into which a motion command for a slave unit is inputted while the operating unit is held by the operator without changing a pose of the operating unit.

5 Claims, 11 Drawing Sheets

Related U.S. Application Data

(60) Provisional application No. 61/806,507, filed on Mar. 29, 2013.

(51) Int. Cl.
*B25J 13/02* (2006.01)
*A61B 1/005* (2006.01)
*A61B 1/04* (2006.01)
*A61B 19/00* (2006.01)
*A61B 34/37* (2016.01)
*A61B 34/00* (2016.01)
*A61B 90/00* (2016.01)
*A61B 34/30* (2016.01)

(52) U.S. Cl.
CPC ............ *A61B 1/00149* (2013.01); *A61B 1/04* (2013.01); *A61B 19/2203* (2013.01); *A61B 34/30* (2016.02); *A61B 34/37* (2016.02); *A61B 34/74* (2016.02); *B25J 3/04* (2013.01); *B25J 13/02* (2013.01); *A61B 2019/2211* (2013.01); *A61B 2019/2223* (2013.01); *A61B 2019/2269* (2013.01); *A61B 2019/464* (2013.01); *A61B 2034/301* (2016.02); *A61B 2090/064* (2016.02)

(58) Field of Classification Search
CPC .. A61B 2017/00296; A61B 2017/0034; A61B 34/37; A61B 34/70; A61B 34/74; A61B 2034/301; A61B 2034/742
USPC .......................................... 600/102; 700/264
See application file for complete search history.

(56) References Cited

U.S. PATENT DOCUMENTS

| | | | | |
|---|---|---|---|---|
| 6,714,841 | B1* | 3/2004 | Wright | A61B 1/00039 600/118 |
| 7,074,179 | B2* | 7/2006 | Wang | A61B 34/75 414/2 |
| 2007/0078565 | A1* | 4/2007 | Ghodoussi | G06F 19/3437 700/245 |
| 2008/0287963 | A1* | 11/2008 | Rogers | A61B 1/00039 606/130 |
| 2009/0118575 | A1* | 5/2009 | Ichikawa | A61B 1/00133 600/103 |
| 2009/0287043 | A1* | 11/2009 | Naito | A61B 1/0052 600/104 |
| 2009/0299136 | A1* | 12/2009 | Hasegawa | A61B 1/0051 600/106 |
| 2009/0326319 | A1* | 12/2009 | Takahashi | A61B 17/00234 600/106 |
| 2010/0022825 | A1* | 1/2010 | Yoshie | A61B 1/00133 600/104 |
| 2010/0081874 | A1* | 4/2010 | Miyamoto | A61B 1/00087 600/109 |
| 2010/0274087 | A1* | 10/2010 | Diolaiti | A61B 1/00087 600/118 |
| 2010/0318100 | A1* | 12/2010 | Okamoto | A61B 1/0052 606/130 |
| 2011/0245844 | A1* | 10/2011 | Jinno | A61B 34/71 606/130 |
| 2013/0310639 | A1* | 11/2013 | Omori | A61B 1/00149 600/102 |
| 2014/0190305 | A1* | 7/2014 | Okamoto | B25J 18/06 74/490.04 |
| 2014/0296633 | A1* | 10/2014 | Gumbs | A61B 1/0052 600/109 |
| 2015/0342442 | A1* | 12/2015 | Tadano | A61B 1/00149 600/102 |
| 2017/0129108 | A1* | 5/2017 | Diolaiti | B25J 13/065 |

FOREIGN PATENT DOCUMENTS

| | | |
|---|---|---|
| JP | 2005-312919 A | 11/2005 |
| JP | 4608601 B2 | 1/2011 |
| JP | 2011-206312 A | 10/2011 |
| JP | 2012-055996 A | 3/2012 |
| WO | WO 01/21056 A2 | 3/2001 |

* cited by examiner

MASTER-SLAVE SYSTEM FOR MOVING SLAVE UNIT BASED ON MOTION COMMANDS INPUTTED INTO TWO COMMAND INPUT UNITS HELD BY EACH HAND OF OPERATOR

CROSS-REFERENCE TO RELATED APPLICATIONS

This application is a Continuation Application of International Application PCT/JP2014/051292 filed on Jan. 22, 2014, which claims priority to U.S. Provisional Patent Application No. 61/806,507 filed on Mar. 29, 2013. The Contents of International Application PCT/JP2014/051292 and U.S. Provisional Patent Application No. 61/806,507 are hereby incorporated by reference herein in its entirety.

TECHNICAL FIELD

The present invention relates to a master-slave system.

BACKGROUND ART

As conventional master input devices of master-slave systems, there have been known devices having similar figures to slave units (see PTL 1, for example).

In a master-slave system of PTL 1, a slave unit is an endoscope including an observation optical system and two treatment tools at a front end surface of a long inserting part, and master apparatus includes: plural joints bringing a corresponding bending portions of the inserting part to perform a bending motion; a handle bringing the inserting part to perform a twist motion through a rotational motion of the handle; and two grips that are disposed at a front end of the handle, having similar figures to treatment tools and being operated by both hands so as to move the two treatment tools.

CITATION LIST

Patent Literature

{PTL 1}
The Publication of Japanese Patent No. 4608601

SUMMARY OF INVENTION

Technical Problem

Unfortunately, in the master-slave system of PTL 1, if the handle of the master apparatus is so operated as to allow the slave unit to be rotationally moved, the observation optical system provided on the front end surface of the inserting part on which the treatment tools are provided is simultaneously rotated; therefore, there is an inconvenience that a position of the handle of the master apparatus deviates from a position of the treatment tools on a monitor screen. Specifically, even if the front end surface is rotated by rotation of the handle, a relative positional relation between the observation optical system and the treatment tools that are provided on the front surface is not changed, and thus the position of the treatment tools is always never changed on an image acquired by the observation optical system and displayed on the monitor screen; consequently, the position of the handle and the position of the treatment tools on the monitor screen deviate from each other.

It may be considered to provide a master apparatus for operating a front end of the slave unit other than the master apparatus for manipulating the treatment tools, but it is required to exchange one master apparatus to the other master apparatus every time the operation is switched over, which makes the work tedious and complex.

An object of the present invention, which has been made in order to solve the above problems, is to provide a master-slave system capable of operating a slave unit without exchanging one master apparatus to the other master apparatus, and capable of maintaining a correspondence relation between a position of the master apparatus and a position of treatment tools on a monitor screen even after the slave unit is operated.

Solution to Problem

In order to attain the above object, the present invention provides the following solutions.

One aspect of the present invention provides a master-slave system including: a slave unit including an observation optical system imaging a subject, and a treatment part projecting from a surface on which the observation optical system is provided, at least part of the treatment part being imaged along with the subject by the observation optical system; a master apparatus including an operating unit held and operated by an operator; a control unit associating operation of the operating unit of the master apparatus with motion of the slave unit and motion of the treatment part; and a monitor screen displaying an image acquired by the observation optical system, wherein the operating unit includes a command input unit into which a motion command for the slave unit is inputted while the operating unit is held by the operator without changing a pose of the operating unit.

DESCRIPTION OF EMBODIMENTS

A master-slave system 1 according to one embodiment of the present invention will be explained with reference to drawings, hereinafter.

Figure 1:
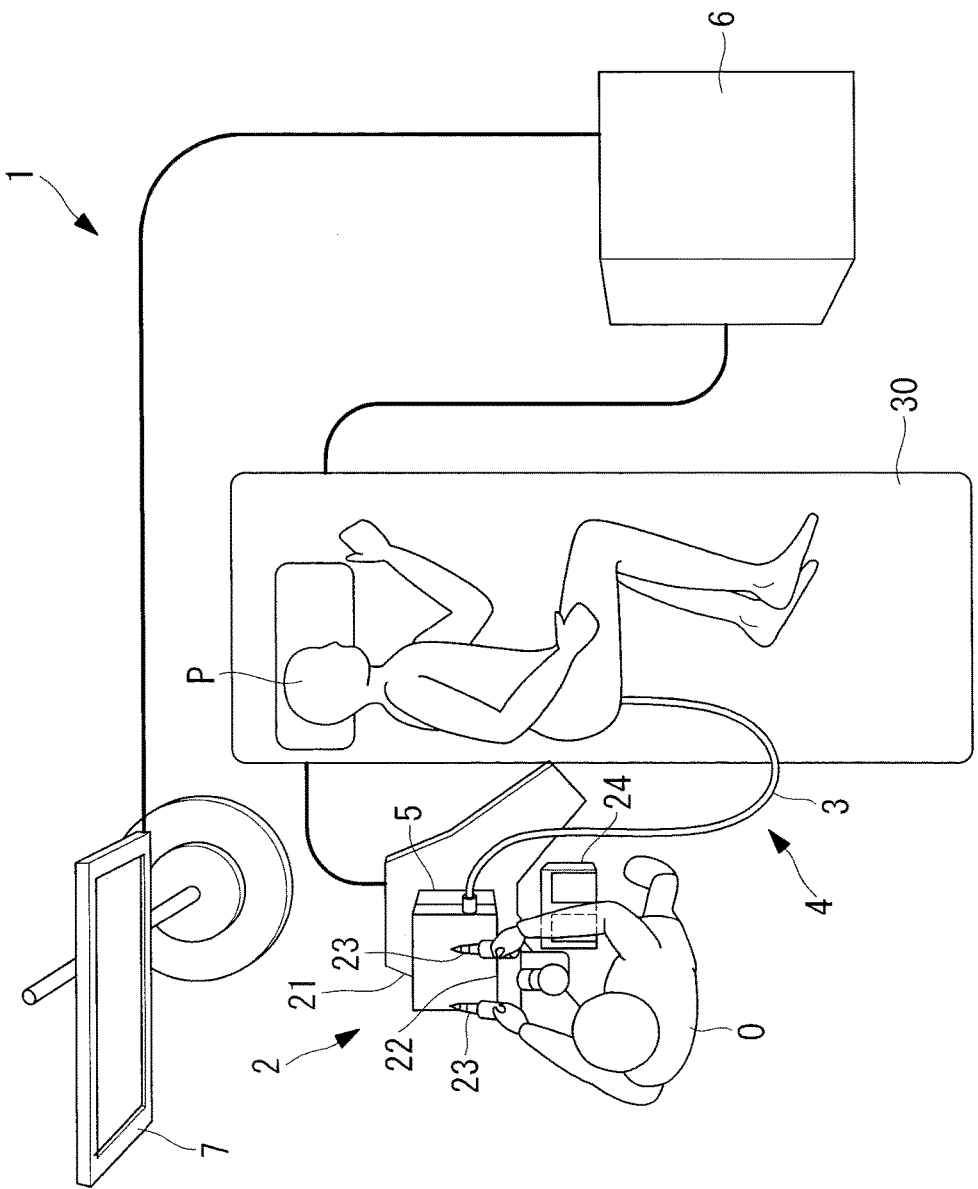
FIG. 1 is a configuration drawing showing an outline of a master-slave system according to one embodiment of the present invention.

The master-slave system 1 according to the present embodiment is an endoscope system as shown in FIG. 1 and includes: a master apparatus 2 operated by an operator O; an endoscope 4 as a slave unit; a driving unit 5 driving the endoscope 4; a control unit 6 controlling the driving unit 5; and a display unit (monitor screen) 7 displaying an image acquired by the endoscope 4.

The endoscope 4 includes a soft and flexible inserting part 3 to be inserted into a body, for example, a soft organ such as the colon, of a patient P.

Figure 2:
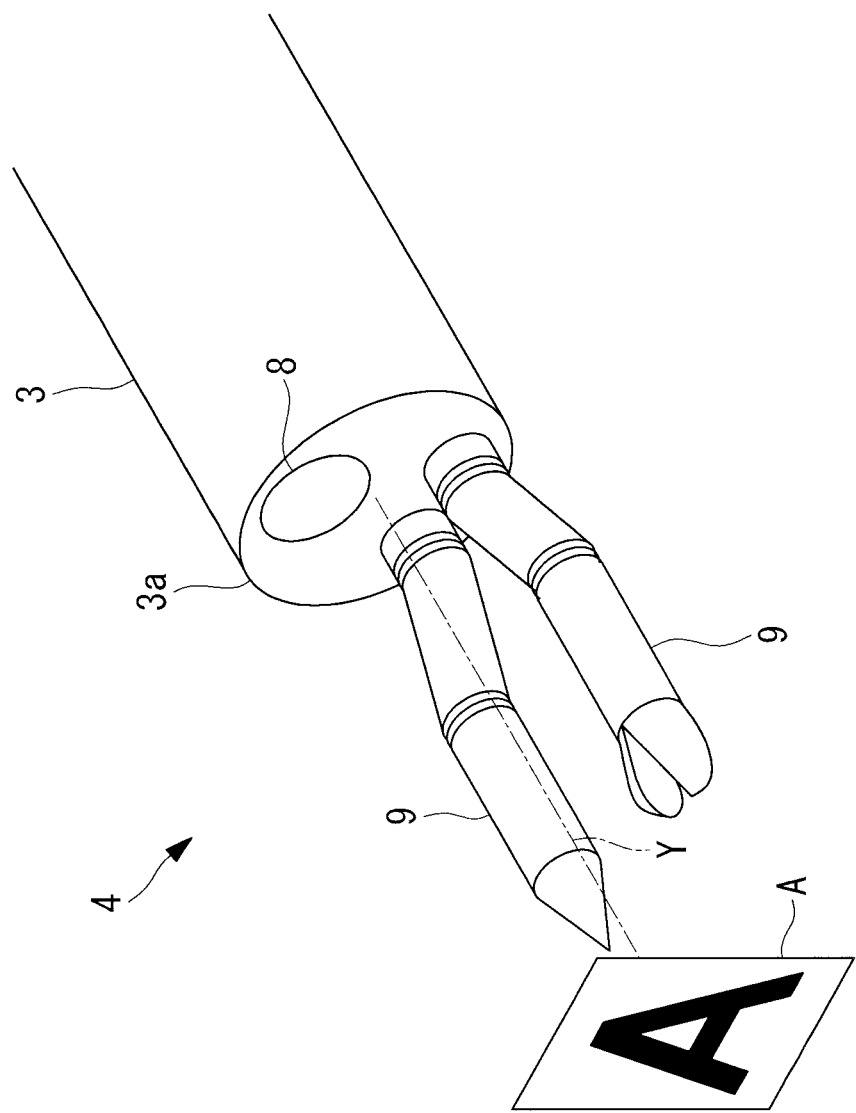
FIG. 2 is a perspective view showing a front end of an inserting part of an endoscope that is a slave unit of the master-slave system in FIG. 1.
Figure 3:
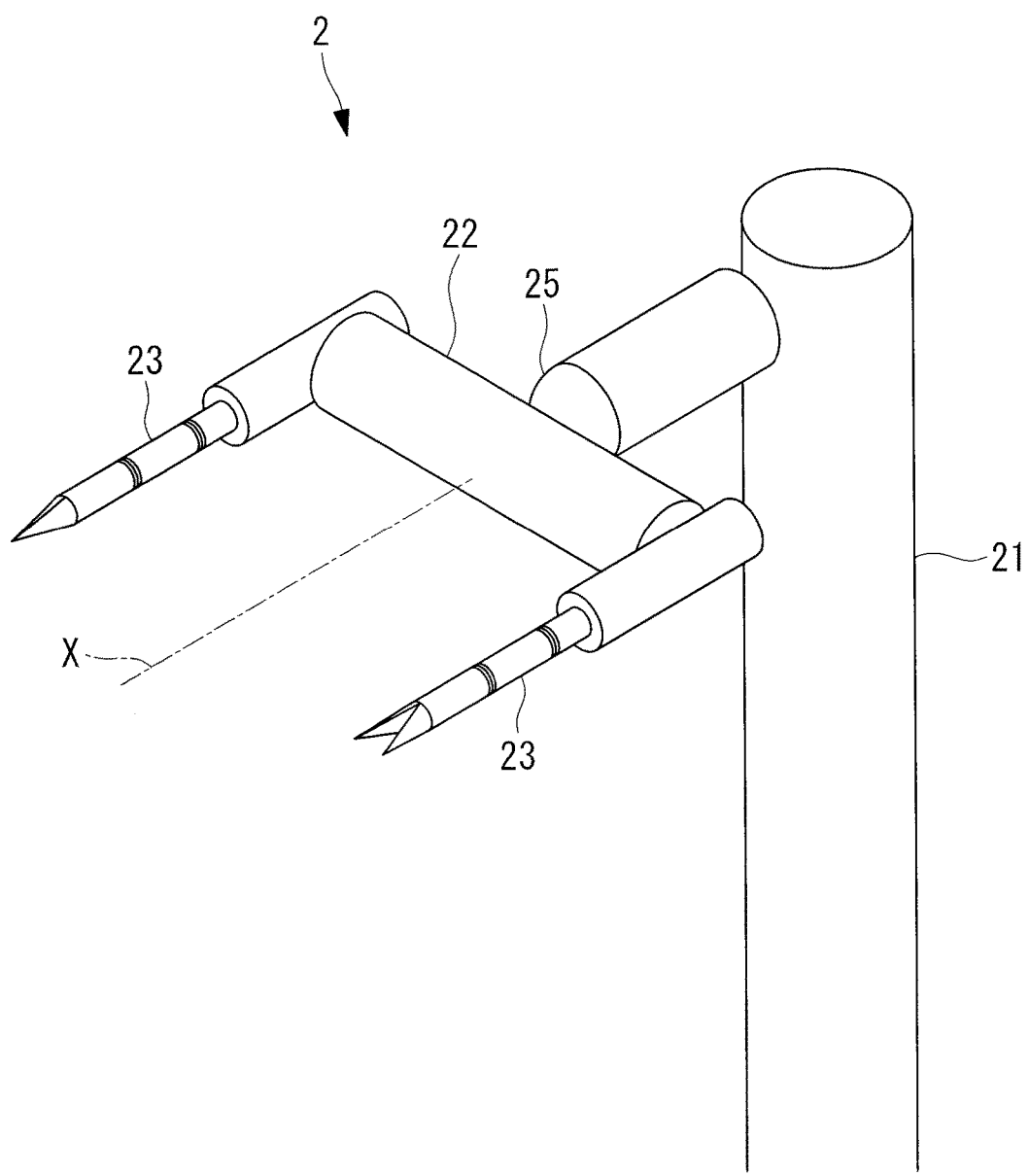
FIG. 3 is a perspective view showing a master apparatus of the master-slave system in FIG. 1.

As shown in FIG. 2, a front end surface 3a of the inserting part 3 is provided with an objective lens 8 of an observation optical system, and two treatment tools (treatment part) 9 projecting frontward from the front end surface 3a. Each of the treatment tools 9 has an articulated structure. Plural bending portions (not shown in the drawing) are provided at the vicinity of the front end of the inserting part 3. A combination of bending of the respective bending portions enables the front end surface 3a of the inserting part 3 to move in any direction.

On a base end side of the inserting part 3, the driving unit 5 drives various motions, such as an inserting motion of the inserting part 3 of the endoscope 4, a bending motion of the inserting part 3, and a twisting motion of the inserting part 3.

The master apparatus 2 according to the present embodiment includes: a handle (operating unit) 22 attached to an operating stand 21 fixed on a floor surface; treatment operating parts (operating unit) 23 having an articulated structure corresponding to treatment tools 9 provided on the right and the left of the handle 22 so that the operator O holds each of front end portions thereof by each hand of the operator for performing the operation; and a foot switch 24 disposed on a floor surface. There is provided, between the operating stand 21 and the handle 22, a force sensor 25 to detect a force applied to the handle 22 in 6 axial directions.

As shown in FIG. 1, a helper (not shown) helps the patient P to lie down on an operating table 30 located on the master apparatus 2 side, and provides appropriate treatment such as disinfection and anesthetizing.

The operator O instructs the helper to introduce the inserting part 3 of the endoscope 4 from an anus into the colon of the patient P. The operator O operates the master apparatus 2 in a manner as to appropriately bend the bending portions of the inserting part 3, thereby moving the front end of the endoscope 4.

The control unit 6 associates a direction of a force applied to the handle 22 of the master apparatus 2 around the horizontal axis X with a rotational direction around the longitudinal axis Y of the front end surface 3a of the inserting part 3, and the control unit 6 also associates a time duration of applying the force with a rotation angle.

In addition, the control unit 6 associates operation of the treatment operating parts 23 of the master apparatus 2 with motion of the treatment tools 9. Associating operation with motion means that operation of the master apparatus 2 side causes a corresponding part of the endoscope 4 to be moved.

Specifically, the control unit 6 generates a rotation command signal regarding rotation around the longitudinal axis Y of the inserting part 3 in accordance with a force applied to the handle 22, and outputs this command signal to the driving unit 5. The control unit 6 generates a rotation command signal regarding respective corresponding joints of the treatment tools 9 in accordance with the rotation angle of the respective joints of the treatment operating parts 23 defined by operating the treatment operating parts 23, and outputs this command signal to the driving unit 5.

In the present embodiment, for example, when a motion mode of the treatment tools is selected by stepping the foot switch 24, the control unit 6 controls respective joints of the treatment operating parts 23 to flexibly swing in accordance with operation by the operator O, thereby moving respective corresponding joints of the treatment tools 9 in accordance with the rotation angle of the respective joints of the treatment operating parts 23. Meanwhile, when a motion mode of the endoscope is selected by stepping the foot switch 24, the control unit 6 controls such that motion of respective joints of the treatment operating parts 23 is fixed by a motor or a brake which are not shown, so that a force applied by the operator O while the operator O holds the treatment operating parts 23 is directly transmitted to the handle 22.

Operation of the above configured master-slave system 1 according to the present embodiment will be explained, hereinafter.

In order to perform observation and treatment inside the body of the patient P using the master-slave system 1 according to the present embodiment, with the inserting part 3 of the endoscope 4 inserted into a body cavity while the operator O observes a state of the body cavity imaged by the observation optical system via the objective lens 8 of the endoscope 4 on the monitor screen 7, the operator O holds the treatment operating parts 23 of the master apparatus 2 and manipulates the handle 22 and the treatment operating parts 23.

In this manner, the inserting part 3 and the treatment tools 9 of the endoscope 4 that is the slave unit are moved.

Figure 6:
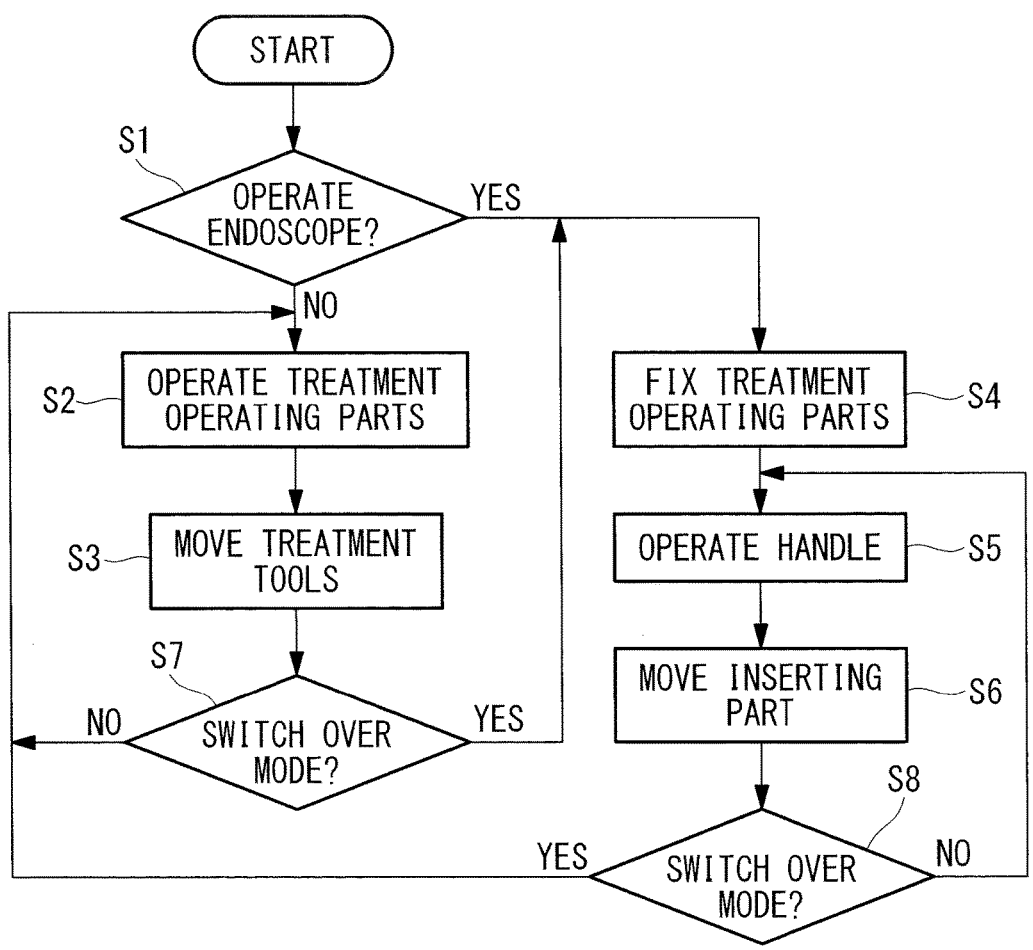
FIG. 6 is a flow chart explaining operation of the master-slave system in FIG. 1.

In order to provide treatment to an affected part or the like using the treatment tools 9, as shown in FIG. 6, the foot switch 24 is stepped to select a treatment tool operating mode (step S1), the two treatment operating parts 23 held by both hands are operated (step S2), so as to move the treatment tools 9 by the control unit 6 (step S3), thereby providing the treatment.

Meanwhile, in order to move the inserting part 3 of the endoscope 4, an endoscope operating mode is selected (step S1), and respective joints of the treatment operating parts 23 is fixed at its current position. Through this work, a force applied by both hands of the operator O who holds the treatment operating parts 23 is directly transmitted to the handle 22.

Figure 4A:
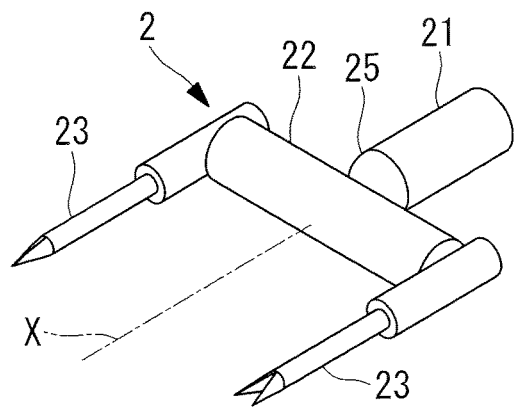
FIG. 4A is a respective drawing of the master apparatus, B the slave unit, and C an image on a monitor screen, in a state in which the master-slave system in FIG. 1 is located at a reference position.
Figure 4B:
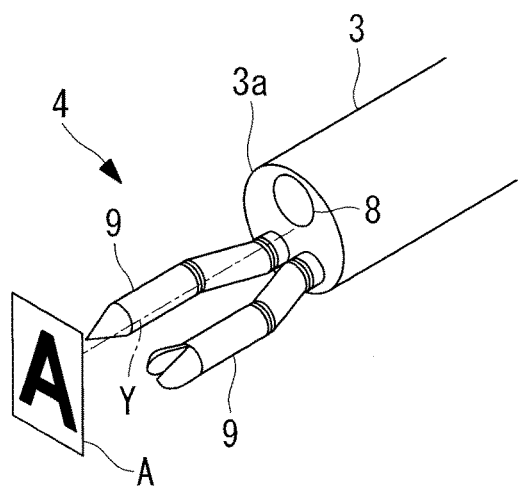
FIG. 4B is a respective drawing of the slave unit in a state in which the master-slave system in FIG. 1 is located at a reference position.
Figure 4C:
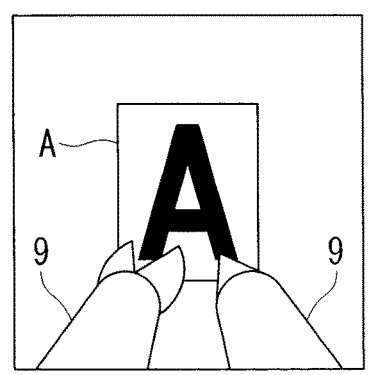
FIG. 4C is a respective drawing of an image on a monitor screen in a state in which the master-slave system in FIG. 1 is located at a reference position.
Figure 5A:
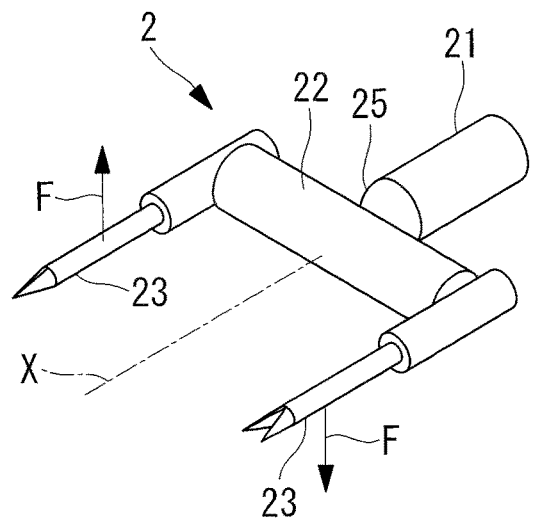
FIG. 5A is a respective drawing showing the master apparatus in a state in which a force is applied to a handle of the master apparatus of the master-slave system in FIG. 1.

For example, from a state in which no force is applied to the handle 22 and the treatment tools 9 as shown in FIG. 4A to FIG. 4(c), a force F is applied to the handle 22 for any period (step S5) as shown in FIG. 5A. The force applied to the handle 22 is detected by a 6-axis force sensor 25 provided between the handle 22 and the operating stand 21.

Figure 5B:
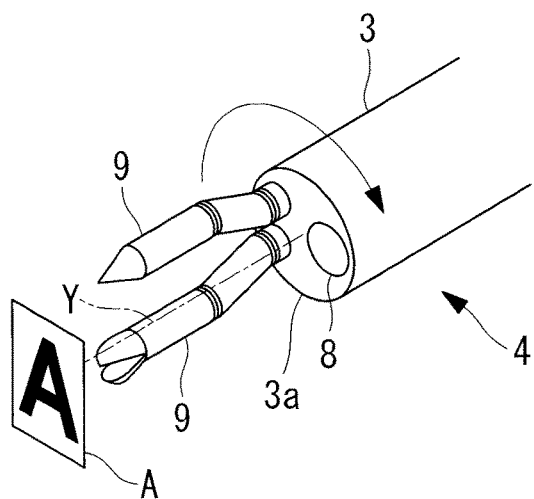
FIG. 5B is a respective drawing showing the slave unit in a state in which a force is applied to a handle of the master apparatus of the master-slave system in FIG. 1.

The control unit 6 moves the respective bending portions of the inserting part 3 of the endoscope 4 in accordance with the direction of the force and the time spent for applying the force that are detected by the force sensor 25 (step S6). In particular, as shown in FIG. 5A, if a force component generating a moment around the horizontal axis X relative to the handle 22 is detected by the force sensor 25, the front end surface 3a of the inserting part 3 is rotated around its longitudinal axis Y in a direction corresponding to the direction of the above detected moment, by an angle corresponding to the above time spent for applying the force, as shown in FIG. 5B.

If the front end surface 3a is rotated, the objective lens 8 and the treatment tools 9 that are provided on the front end surface 3a are also rotated in the same direction at the same time.

Figure 5C:
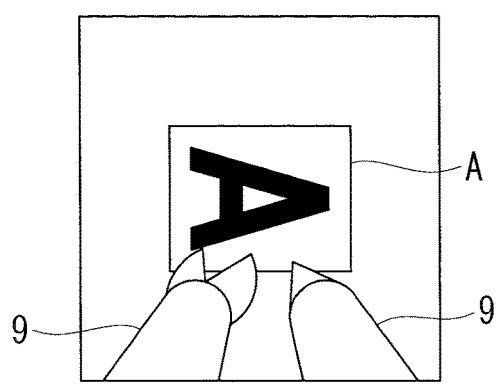
FIG. 5C is a respective drawing showing an image on the monitor screen in a state in which a force is applied to a handle of the master apparatus of the master-slave system in FIG. 1.

If the objective lens 8 is rotated, its visual field is also rotated; therefore, as shown in FIG. 5(c), a subject A in an acquired image is rotated in a reverse direction to the rotation direction of the visual filed at the same rotation angle. The relative relational position between the objective lens 8 and the treatment tools 9 both of which are disposed on the same front end surface 3a is never changed, and thus the position of the treatment tools 9 partially displayed in the acquired image is never changed. If it is desired to optionally switch over the mode between the endoscope operating mode and the treatment tool operating mode, the foot switch 24 may be stepped to switch over the mode at step S1 and step S8.

As aforementioned, according to the master-slave system 1 of the present embodiment, when the front end surface 3a of the inserting part 3 is so rotated as to change the direction of the treatment tools 9 relative to the subject A, it is configured to rotate the front end surface 3a by the direction of applying the force to the handle 22 without rotating the handle 22; therefore, the position of the treatment operating parts 23 held by the operator O and the position of the treatment tools 9 displayed on the monitor screen 7 are never moved, but stay at the same positions all the time.

Specifically, in the present embodiment, if the operator O applies a counterclockwise moment to the handle 22, the subject A is rotated in the clockwise direction on the monitor screen 7. At this time, the position of the handle 22 and the position of the treatment tools 9 on the monitor screen 7 are never changed; thus there is an advantage that the operator O who provides treatment while watching the monitor screen 7 can perform an intuitive operation. In addition, the position of the handle 22 and the position of the treatment part 9 on the monitor screen 7 are always correspondent to each other; therefore, there is another advantage that even if the operator O is once left the place after the operation, and then resumes the operation after a while, the operator O can readily recognize the correspondence relation between the handle 22 and the treatment part 9.

In the present embodiment, the 6-axis force sensor 25 is provided between the handle 22 and the operating stand 21, so that a force applied by the operator O is detected by the force sensor 25 via the treatment operating parts 23 held by the operator O and the handle 22 connected to the treatment operating parts 23; but instead of this configuration, the force sensor 25 may be provided to the joint part disposed at the front end of the treatment operating parts 23. With this configuration, it is possible to detect the force applied by the operator O in a more direct manner. In this case, it is required to determine whether or not the force is a force component rotating the handle 22, based on the direction to which the joint part disposed at the front end of the treatment operating parts 23 is orientated. In this case, a pose of the joint part disposed at the front end may be acquired and converted into coordinates.

Other than the rotational operation of the inserting part 3 of the endoscope 4 that is the slave unit, for example, the frontward and backward direction in the Y axial direction of the inserting part 3 may be moved by a force input in the X axial direction of the master apparatus 2, or a force input in the right and left direction or in the up and down direction may be associated with motion at a bending angle of the front end of the inserting part 3. In this case also, the endoscope 4 can be moved by the master apparatus 2 without deviating the positional relation between the treatment operating parts 23 of the master apparatus 2 and the treatment tools 9 displayed on the monitor screen 7.

Figure 7:
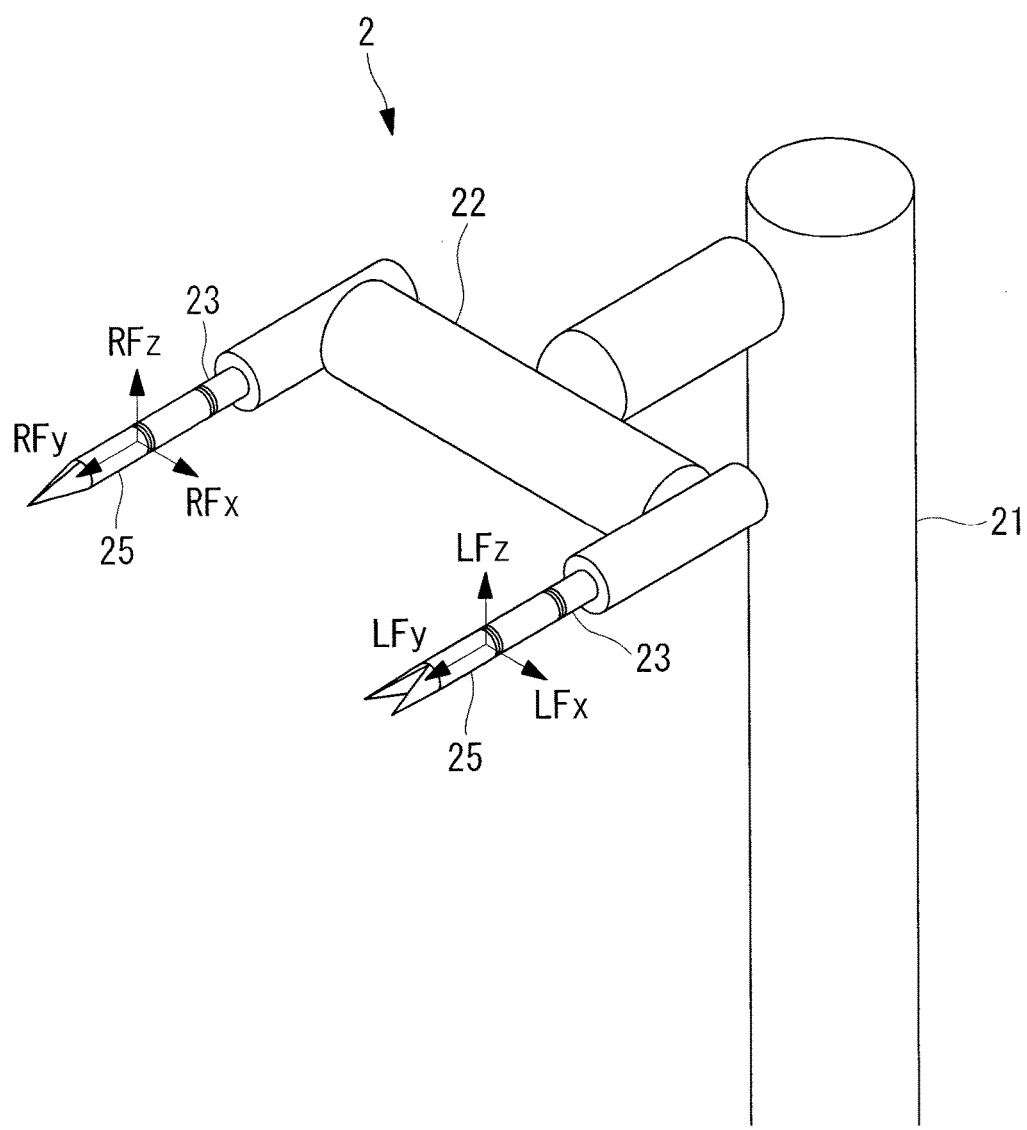
FIG. 7 is a perspective view showing the master apparatus in a modification of the master-slave system in FIG. 1.

As shown in FIG. 7, the force sensor 25 may be provided to each of the two treatment operating parts 23 held by both right and left hands.

In this case, if forces in the same direction are detected by the two force sensors 25, an average value of the detected forces may be used as amount of operation. Through this configuration, it is possible to secure more stable operation. If forces detected by the two force sensors 25 are greatly different from each other, it may be determined that there is any abnormality.

In the case of providing the force sensor 25 to each of the two treatment operating parts 23, it may be configured, as shown in FIG. 7, to provide the force sensors 25 that can respectively detect a force in 3 axial directions: LFx, LFy, LFz, and a force in 3 axial directions: RFx, RFy, RFz. Through this configuration, a motion command with 6 degrees of freedom can be obtained by adding the both, also new motion commands may be obtained in combination of the both (a sum total).

For example, if it is assumed that a force applied to the treatment operating part 23 held by the right hand is defined to be RFx, RFy, RFz, and a force applied to the treatment operating part 23 held by the left hand is defined to be LFx, LFy, LFz, there may be provide a motion command to bring the observation optical system to zoom in if RFx>0 and LFx<0, and to bring the observation optical system to zoom out if RFx<0 and LFx>0. Zooming may be carried out by optical zooming, digital zooming, or by moving the inserting part of the slave unit in forward and backward in the Y axial direction.

In the case of requiring operation by both hands, if two slave units are operated as motion targets, and a force is detected by only one of the force sensors 25, no motion command may be generated, or it may be notified that the other force sensor 25 is in trouble.

In combination of these two force sensors in the above manner, for example, if using 3-axis force sensors 25, a 3-axis moment in addition to a 3-axis force enables a 6-axis input in total. In other words, there are advantages that force sensors 25 with the same number or fewer axes than the number of axes required to be inputted can be used, thereby configuring the sensors with less cost and attaining duplication of the force sensors 25.

This is similar to the case of using 3-or-fewer-axis sensors, and a combination of two 2-axis sensors enables a 4-axis input including a moment, or a combination of two 1-axis sensors enables a 2-axis input.

As aforementioned, the case of using 3-or-fewer-axis sensors has been exemplified, but two 4-axis or more sensors may be combined, thereby attaining an 8-axis or more input.

Figure 8:
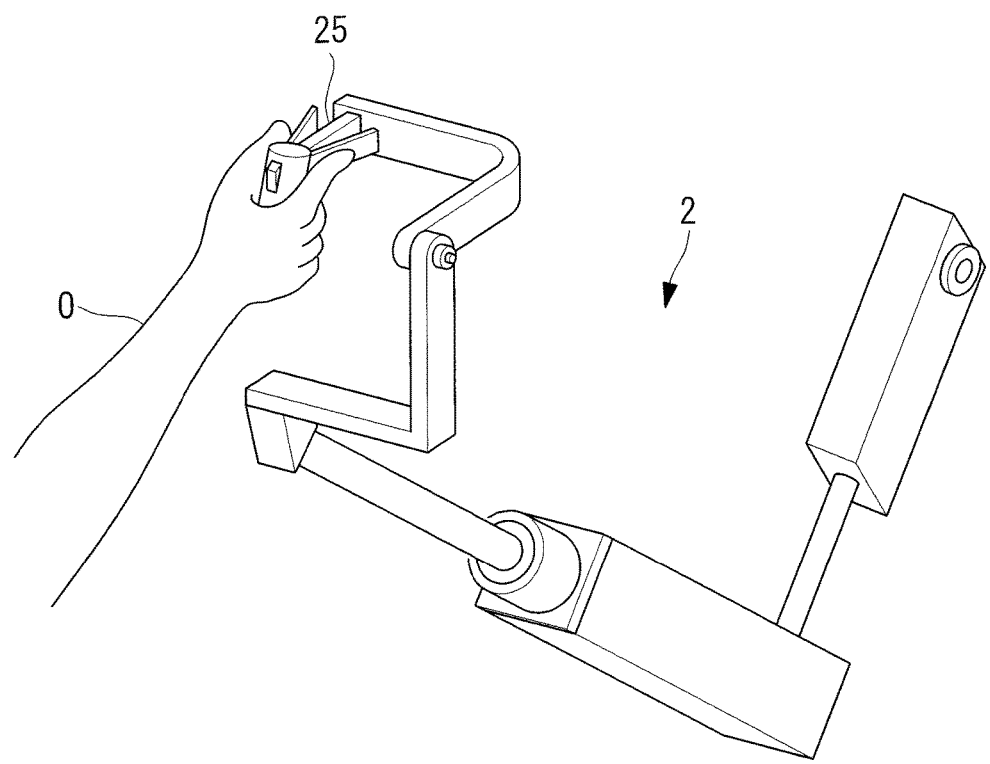
FIG. 8 is a perspective view showing the master apparatus in another modification of the master-slave system in FIG. 1.
Figure 9A:
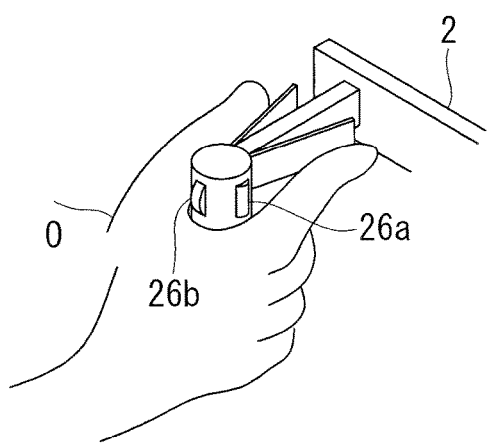
FIG. 9A is a perspective view showing modifications of a command input unit provided to the master-slave system in FIG. 1, and showing dials provided to the operating unit and operated by a dial.
Figure 9B:
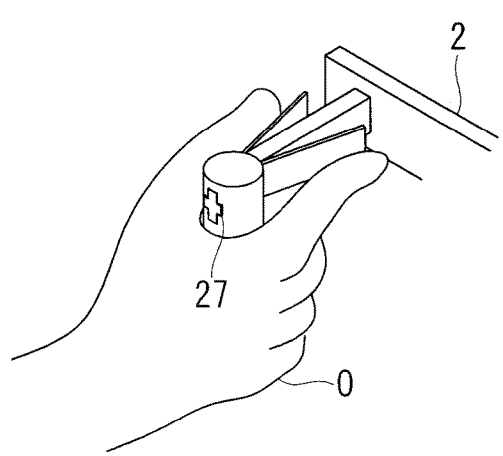
FIG. 9B is a perspective view showing modifications of a command input unit provided to the master-slave system in FIG. 1, and showing dials provided to the operating unit and operated by a cross key.
Figure 9C:
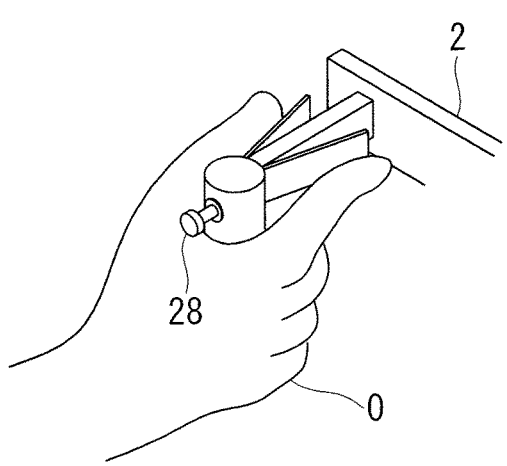
FIG. 9C is a perspective view showing modifications of a command input unit provided to the master-slave system in FIG. 1, and showing dials provided to the operating unit and operated by a joystick.
Figure 9D:
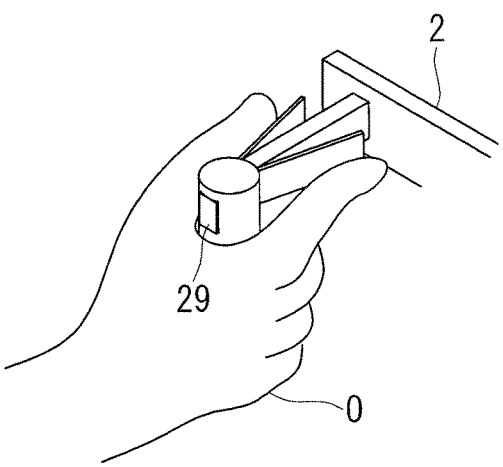
FIG. 9D is a perspective view showing modifications of a command input unit provided to the master-slave system in FIG. 1, and showing dials provided to the operating unit and operated by a touch panel.
Figure 9E:
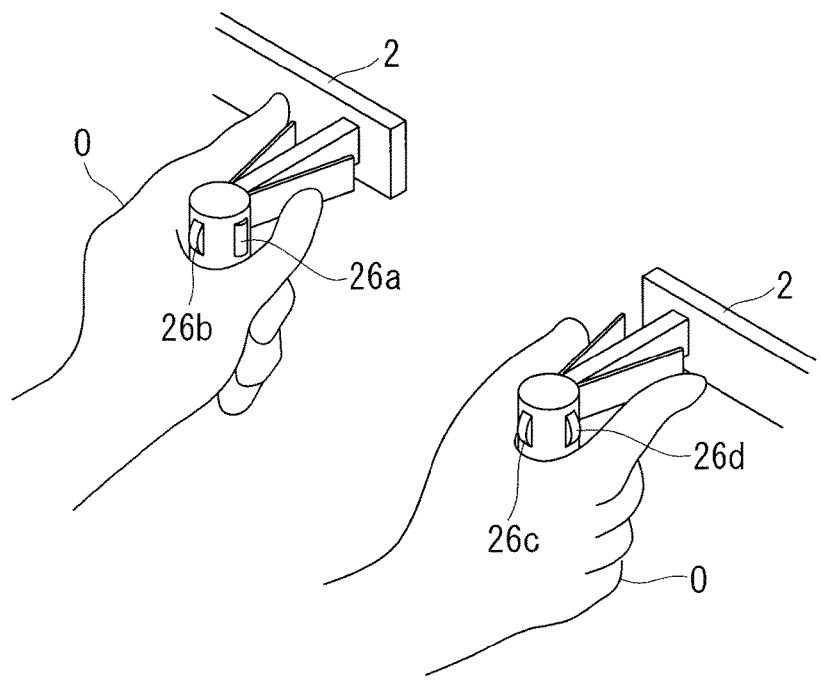
FIG. 9E is a perspective view showing modifications of a command input unit provided to the master-slave system in FIG. 1, and showing dials provided to the operating unit and operated by both hands.

As shown in FIG. 8, in the case of using the master apparatus 2 of a different type, it is preferable to provide the force sensor 25 in the vicinity of a position where the operator O holds the handle to apply the force F.

In the present embodiment, the force sensor 25 has been exemplified as a command input unit; but instead of this, as shown in FIG. 9, there may be employed an input device operable with fingers other than the fingers holding the treatment operating parts 23, for example, such as A a dial 26a in the right and left direction and a dial 26b in the up and down direction, B a cross key 27, C a joystick 28, and D a touch panel 29. As shown in FIG. 9E, the operation may be allocated by input devices, such as the dial 26a in the right and left direction, the dial 26b in the up and down direction, a dial 26c in the frontward and backward direction, and a dial 26d in the roll direction, the dials being disposed at the right and left side of the treatment operating parts 23.

Figure 10:
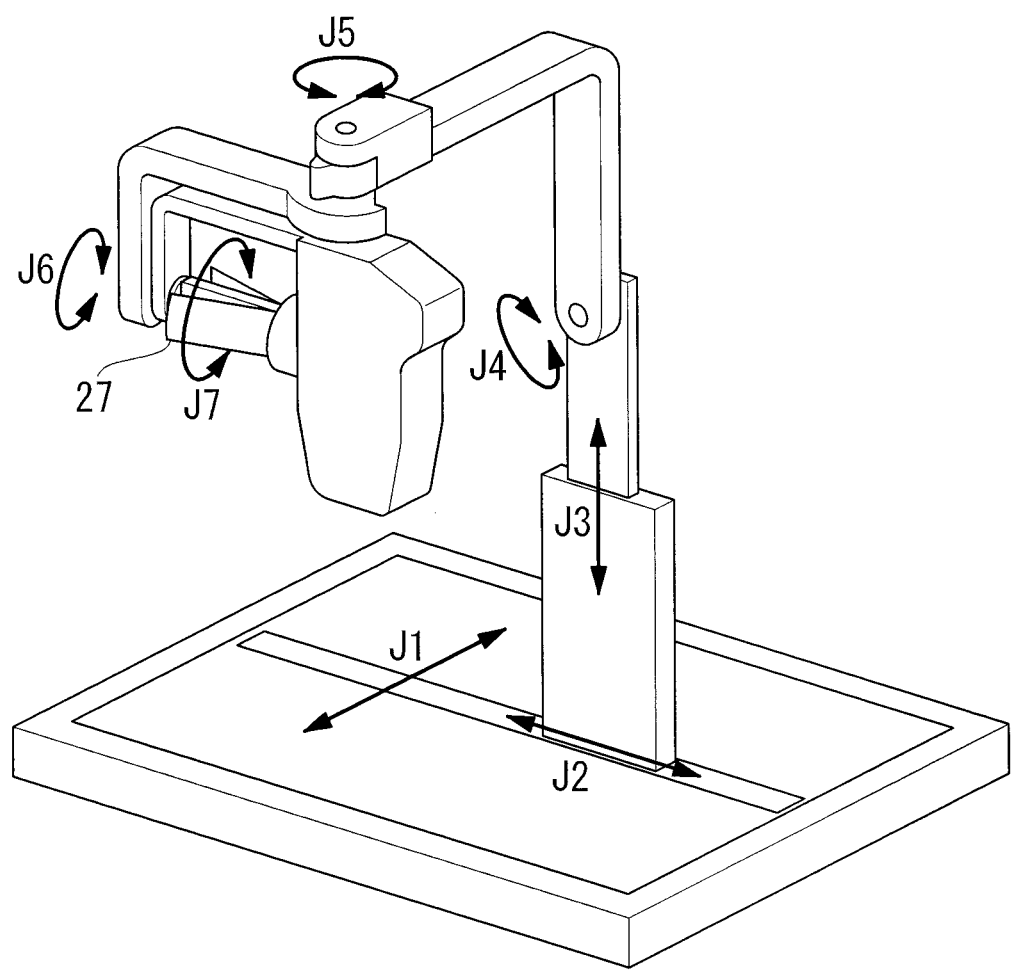
FIG. 10 is a perspective view showing the master apparatus in another modification of the master-slave system in FIG. 1.

As shown in FIG. 9, it may be configured to provide the master apparatus 2 with joints whose number is equal to or more than the number of joints of the endoscope that is the slave unit, whereby motions of the redundant joints are allocated to a rotation command regarding rotation around the longitudinal axis Y of the front end surface 3a of the inserting part 3 of the endoscope 4. In an example of FIG. 10, a grip 27 at a forefront end held by the fingers of the operator O is further provided with redundant joints allowing the grip to be rotated around a longitudinal axis J7, and the front end surface 3a of the inserting part 3 is rotated by the motion of these joints. Reference numerals J1 to J6 denote respective joint axes provided to the master apparatus 2 for the sake of moving the front end surface 3a of the inserting part 3 with 6 degrees of freedom.

Figure 11A:
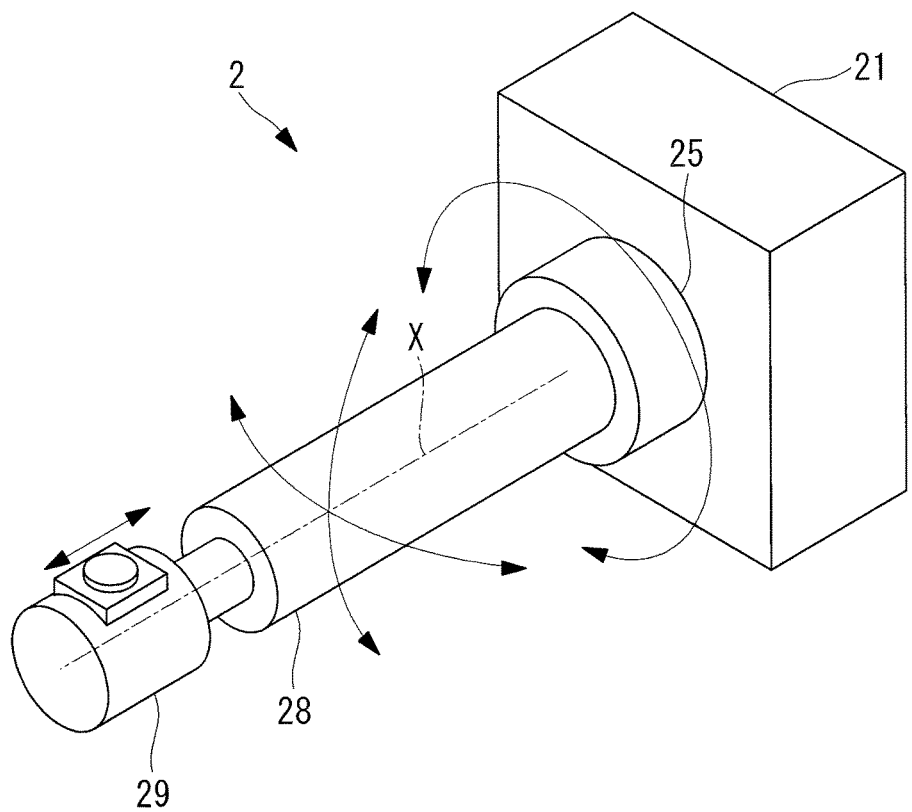
FIG. 11A is a perspective view showing the master apparatus in another modification of the master-slave system in FIG. 1.
Figure 11B:
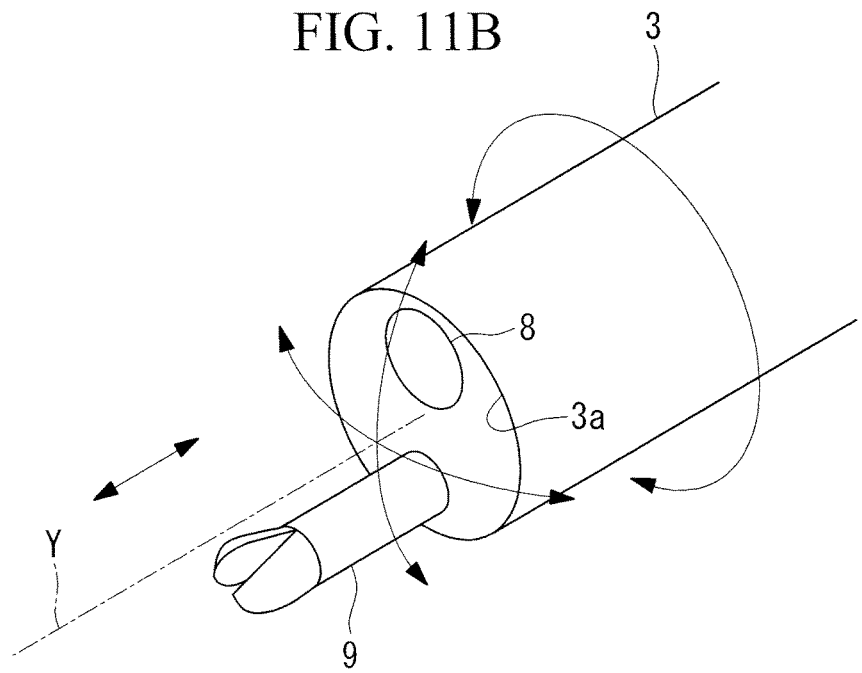
FIG. 11B is a perspective view showing the slave unit in another modification of the master-slave system in FIG. 1.

In the present embodiment, the case of including the two treatment tools 9 projecting from the front end surface 3a of the inserting part 3 has been explained; but instead of this, the present invention may be applicable to a case of including a single treatment tool, as shown in FIG. 11B. In this case, as shown in FIG. 11A, the master apparatus 2 may be configured such that a force is applied in a direction swinging a lever 28 attached to the operating stand 21 via the force sensor 25, thereby generating a motion command to swing a neck of the front end of the inserting part 3 of the endoscope 4 as the slave unit; and a force for rotating the lever 28 around the longitudinal axis X thereof is applied, thereby generating a motion command to rotate the front end surface 3a of the inserting part 3 around the longitudinal axis Y. In addition, a slider 29 may be provided to a front end of the lever 28 so as to change projecting amount of the treatment tools 9 by moving the slider 29 in the longitudinal axis X.

According to the present aspect, if the operating unit of the master apparatus is operated, the control unit rotates the slave unit around an axial line intersecting the surface on which the observation optical system is provided by an angle corresponding to amount of operation of the operating unit, and moves the treatment part. Through the rotation of the slave unit, the observation direction in which the subject is observed by the observation optical system is changed. Because the treatment part projects from the surface on which the observation optical system is provided, the treatment part is also rotated along with the rotation of the observation optical system in the same direction at the same time. With the motion of the treatment part, the subject can be treated by the treatment part from a direction in which the subject is observed by the observation optical system.

In this case, in order to rotate the slave unit, the operator inputs a motion command, for example, a rotation command, by operating a command input unit provided to the operating unit. Hence, the slave unit is rotated around the axial line intersecting the surface on which the observation optical system is provided. When the slave unit is rotated, the observation optical system and the treatment part provided on this surface are rotated in the same direction at the same time, and thus the subject displayed on the monitor screen is rotated, but the treatment part on the monitor screen is never moved.

According to the present aspect, if the slave unit is rotated by operating the command input unit, the pose of the operating unit held by the operator is never changed, so that the pose of the operating unit and the position of the treatment part on the monitor screen are always maintained in the same correspondence relation. Accordingly, the operator who provides treatment while watching the monitor screen can perform an intuitive operation. Since the position of the operating unit is corresponding to the position of the treatment part on the monitor screen, the operator can readily recognize the correspondence relation between the operating unit and the treatment part even if the operator resumes the operation after a while from a previous operation.

In the above aspect, the motion command may be a rotational motion command, and the control unit may associate operation of the operating unit of the master apparatus with rotation of the slave unit around an axial line intersecting the surface and with motion of the treatment part.

Through this configuration, even if the slave unit is rotated, the pose of the operating unit held by the operator is never changed; thus the pose of the operating unit and the position of the treatment part on the monitor screen can always be maintained in the same correspondence relation, so that the operator who provides treatment while watching the monitor screen can perform an intuitive operation.

In the above aspect, the command input unit may be a force sensor that detects a direction of a force applied to the operating unit, and the control unit may determine a motion direction of the slave unit in accordance with the direction of the force detected by the force sensor.

Through this configuration, when the operator who holds the operating unit applies a force onto the operating unit, the direction of the force is detected by the force sensor, and the control unit rotates the slave unit in accordance with the detected direction of the force. Accordingly, while holding the operating unit without displacing the operating unit, it is possible to provide the treatment by intuitively operating the slave unit.

In the above aspect, the command input unit may be an input device disposed at a position where the input device is operable with fingers other than the fingers holding the operating unit.

Through this configuration, while keeping holding the operating unit with any of the fingers without moving the operating unit, the operator can operate the input device with fingers other than the fingers holding the operating unit in a manner as to rotate the slave unit.

In the above aspect, the operating unit may be provided at each of two positions so that each operating unit is held by each hand of the operator, and each operating unit may be provided with the command input unit.

Through this configuration, a rotation command for rotating the slave unit may be allocated and inputted into two command input units. For example, if commands having the same direction are inputted into the two command input units, these commands may be averaged into a rotation command; or if commands inputted into the two command input units are greatly different from each other, it may be determined that there is any abnormality in one of the two command input units.

In the above aspect, the control unit may move the slave unit based on an average value of motion commands inputted into two command input units.

Through this configuration, it is possible to more stably move the slave unit by both hands.

In addition, the control unit may move the slave unit based on a sum total of motion commands inputted into two command input units.

Through this configuration, it is possible to move the slave unit in a pattern in accordance with each combination of motion commands inputted into the two command input units.

In the above aspect, each of the command input units may be a force sensor in 3 axial directions.

Through this configuration, it is possible to command a motion with 6 degrees of freedom of the slave unit by using the two command input units.

Advantageous Effects of Invention

According to the present invention, the following advantageous effects can be attained: it is possible to operate a slave unit without exchanging one master apparatus to the other master apparatus; it is possible to maintain a correspondence relation between a position of the master apparatus and a position of treatment tools on the monitor screen even after the slave unit is operated; and it is possible to maintain the correspondence relation between the position of the master apparatus and the position of the treatment tools on the monitor screen when the slave unit is rotated by operating the master apparatus.

REFERENCE SIGNS LIST

A subject
O operator
Y longitudinal axis (axial line)
1 master-slave system
2 master apparatus
3a front end surface (surface)
4 endoscope (slave unit)
6 control unit
7 monitor screen
8 objective lens (observation optical system)
9 treatment tool (treatment part)
22 handle (operating unit)
23 treatment operating part (operating unit)
25 force sensor (command input unit)
26a, 26b, 26c, 26d dial (input device)
27 cross key (input device)
28 joystick (input device)
29 touch panel (input device)

The invention claimed is:

1. A master-slave system comprising:
a slave unit including an observation optical system imaging a subject, and a treatment part projecting from a surface on which the observation optical system is provided, at least part of the treatment part being imaged along with the subject by the observation optical system;
a master apparatus including an operating unit held and operated by an operator;
a controller associating operation of the operating unit of the master apparatus with motion of the slave unit and motion of the treatment part; and
a monitor screen displaying an image acquired by the observation optical system, wherein
the operating unit includes a command input unit into which a motion command for the slave unit is inputted while the operating unit is held by the operator without changing a pose of the operating unit,
the operating unit is provided at each of two positions so that each operating unit is held by each hand of the operator,
each operating unit is provided with the command input unit, and
the controller moves the slave unit based on an average value of motion commands inputted into two command input units.

2. The master-slave system according to claim 1, wherein the motion command is a rotational motion command, and
the controller associates operation of the operating unit of the master apparatus with rotation around an axial line intersecting the surface of the slave unit and with motion of the treatment part.

3. The master-slave system according to claim 1, wherein each of the two command input units is a force sensor that detects a direction of a force applied to a respective operating unit, and
the controller determines a motion direction of the slave unit in accordance with the direction of the force detected by the force sensors.

4. The master-slave system according to claim 1, wherein each of the two command input units is an input device disposed at a position where the input device is operable with fingers other than the fingers holding the operating unit.

5. The master-slave system according to claim 1, wherein each of the two command input units is a force sensor in 3 or fewer axial directions.

* * * * *